US011389265B2

(12) United States Patent
Steffen et al.

(10) Patent No.: US 11,389,265 B2
(45) Date of Patent: Jul. 19, 2022

(54) SURGICAL MICROSCOPE WITH STAND AND METHOD FOR CONFIGURING A STAND

(71) Applicant: Carl Zeiss Meditec AG, Jena (DE)

(72) Inventors: Joachim Steffen, Westhausen (DE);
Daniel Kolster, Oberkochen (DE);
Andrè Mueller, Koenigsbronn-Zang (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/870,880

(22) Filed: May 8, 2020

(65) Prior Publication Data

US 2020/0352673 A1    Nov. 12, 2020

(30) Foreign Application Priority Data

May 9, 2019    (DE) .................... 10 2019 112 153.1

(51) Int. Cl.
*A61B 90/25*    (2016.01)
*H04N 7/18*    (2006.01)
(Continued)

(52) U.S. Cl.
CPC .......... *A61B 90/25* (2016.02); *H04N 5/2253* (2013.01); *H04N 7/183* (2013.01); *H04N 13/302* (2018.05)

(58) Field of Classification Search
CPC .... A61B 90/25; H04N 13/302; H04N 5/2253; H04N 5/2257; H04N 7/183
See application file for complete search history.

(56) References Cited

U.S. PATENT DOCUMENTS

| 6,364,268 B1 | 4/2002 | Metelski |
| 7,841,979 B2 | 11/2010 | Hirose |

(Continued)

FOREIGN PATENT DOCUMENTS

| EP | 1067419 A1 | 1/2001 |
| JP | H11290339 A | 10/1999 |
| NL | 1039675 C | 12/2013 |

OTHER PUBLICATIONS

Office Action issued in German Patent Application No. DE 10 2019 112 153.1 (from which this application claims priority), dated Feb. 24, 2020 and English language translation thereof.

*Primary Examiner* — Kathleen V Nguyen
(74) *Attorney, Agent, or Firm* — Falk Ewers; Ewers IP Law PLLC

(57) ABSTRACT

A stand for a surgical microscope includes a digiscope and an imaging unit which are interconnected and mounted on an arm of the stand at a joint rotatably about an axis of rotation. The digiscope and the imaging unit are arranged on a bridge such that a fixed spatial relationship, in particular a distance larger than zero between the digiscope and the imaging unit during a relative movement between the digiscope and the patient is maintained. A method for configuring a stand with a bridge includes determining distances between eyes of a surgeon and the imaging unit, between the surgeon and an operating field, between the receptacle of the digiscope and the operating field, and between the imaging unit and the receptacle of the digiscope, and determining a length of the bridge to optimally set a distance from the surgeon to the patient and the imaging unit for the surgeon.

17 Claims, 4 Drawing Sheets

(51) Int. Cl.
*H04N 13/302* (2018.01)
*H04N 5/225* (2006.01)

(56) References Cited

U.S. PATENT DOCUMENTS

| | | |
|---|---|---|
| 2004/0251390 A1 | 12/2004 | Wachob |
| 2006/0102811 A1 | 5/2006 | Musset et al. |
| 2006/0250684 A1 | 11/2006 | Sander |
| 2011/0261184 A1* | 10/2011 | Mason ............... G02B 21/0012 348/79 |
| 2016/0360117 A1* | 12/2016 | Elefteriu ................ A61B 90/20 |
| 2017/0158104 A1* | 6/2017 | Le ...................... B64D 11/0638 |
| 2018/0263723 A1* | 9/2018 | Beaumont ............... A61B 90/50 |
| 2020/0030054 A1* | 1/2020 | Okawara ................ A61C 19/04 |

\* cited by examiner

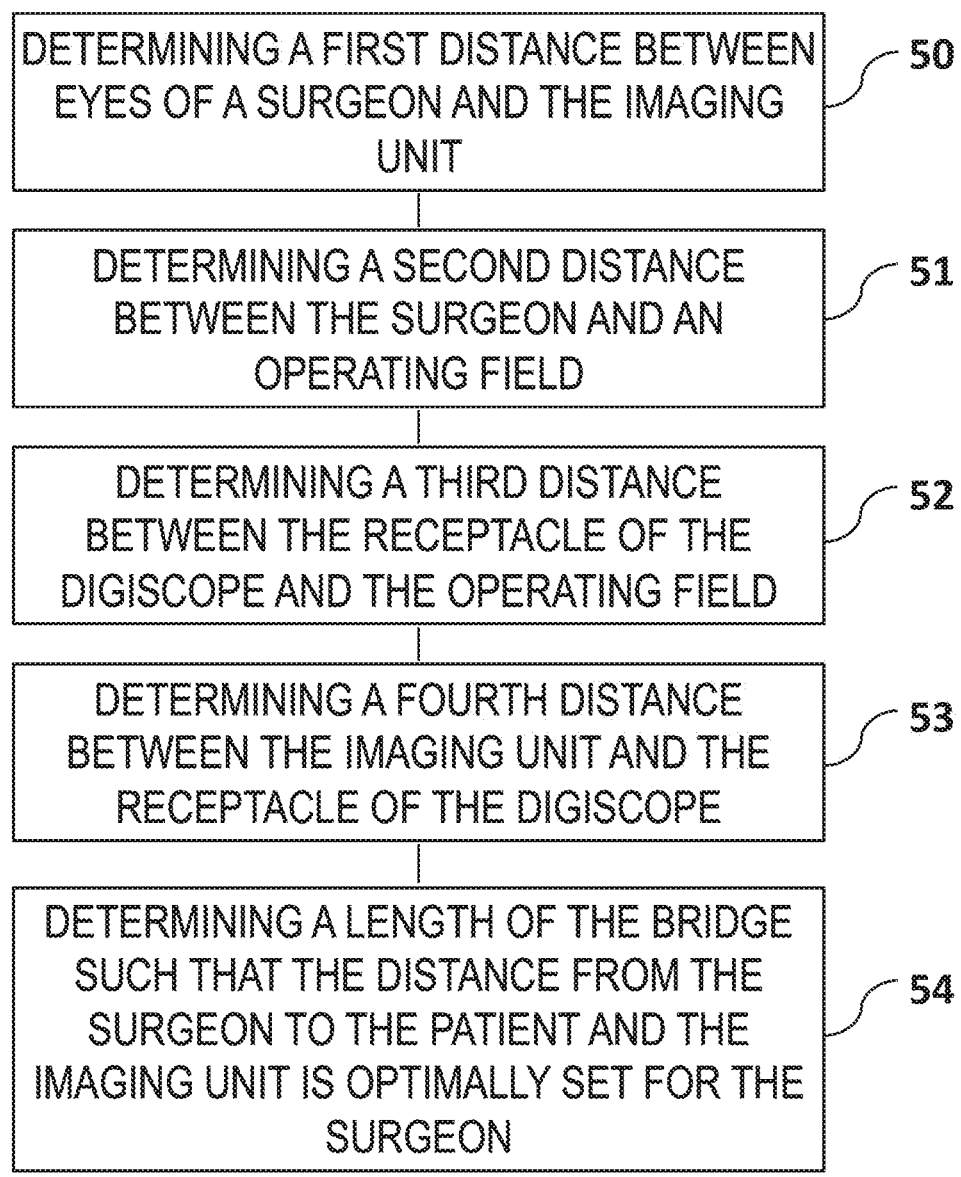

SURGICAL MICROSCOPE WITH STAND AND METHOD FOR CONFIGURING A STAND

CROSS REFERENCE TO RELATED APPLICATIONS

This application claims priority to German patent application DE 10 2019 112 153.1, filed May 9, 2019, the entire content of which is incorporated herein by reference.

TECHNICAL FIELD

The disclosure relates to a surgical microscope with a stand and a method for configuring a stand.

BACKGROUND

In microsurgery and, specifically, in ophthalmology, the eyepieces of the microscope for observing the operating field are being replaced ever more frequently by two video cameras and a stereoscopic screen. In the process, the video cameras record the operating field through the imaging optical unit of the microscope and the stereoscopic screen displays the recorded images. The advantages of these digital microscopes, which are also referred to as digiscopes, include ergonomically improved conditions for the surgeon, multifaceted options for digital image processing and augmenting the image and improved options for the training of future surgeons. Surgical microscopes currently available on the market employ relatively large screens with a size of up to 55". However, these are disadvantageous in that they are located on a separate stand and therefore require a lot of space in the usually small operating theatres. What applies in general is that the 3D impression of a 3D screen is only optimal at a certain relative spatial position, i.e., at a certain distance and at a certain angle in relation to the observer, which is referred to as the "sweet spot". This relative spatial position is set when specifying the screen and is taken into account during the manufacturing process, with the three-dimensional impression of the representation only even being provided in a realistic fashion in a very narrow range around this "sweet spot". During the use of the 3D screen, this distance between the surgeon and the 3D screen and the lateral and vertical angles (swivelling and inclining) of the 3D screen should therefore be maintained as optimally as possible in relation to the viewing direction of the observer.

In the case of cataract operations, in particular, which often only take approximately 15 to 20 minutes, the used apparatuses have to be repositioned relatively frequently with a new patient. The high patient throughput requires this procedure to be at high speed. As a result of arranging the screen on an additional stand, the surgical microscope and the screen have to be moved in order to align the screen at the optimal distance and angle with respect to the surgeon again, affecting the speed of the procedure in disadvantageous fashion.

U.S. Pat. No. 7,841,979 B2 describes an arrangement in which the microscope is connected to the screen by way of a kinematic system. When one of the two elements is moved, the kinematic system moves the other element along. This arrangement is disadvantageous in that a movement of the microscope or of the screen relative to the patient alters the distance between the microscope and the screen, which has a negative effect on the ergonomics and the alignment of the screen with respect to the surgeon, and hence on the image quality.

The patent application NL 1039675 describes a structure in which a microscope is integrated in a screen and securely connected to the latter, and the angle of the microscope is determined by the angle of the screen, which is intended to emulate the view through an eyepiece. A substantial disadvantage of this arrangement consists of either the screen being able to be positioned in an ergonomic position and at an optimum distance from the surgeon or the microscope being able to be advantageously arranged over the operating field, but both of these actions cannot be performed at the same time.

SUMMARY

It is an object of the present disclosure to provide an apparatus which solves the above-described disadvantages of the related art. A further object of the disclosure is to provide a method for configuring such an apparatus.

This object is achieved by a surgical microscope and a method for configuring a surgical microscope as described herein.

A surgical microscope according to an aspect of the disclosure includes a digiscope and an imaging unit, wherein the digiscope and the imaging unit are interconnected and mounted on an arm of a stand, at a first joint so as to be rotatable about an axis of rotation. According to an aspect of the disclosure, the digiscope and the imaging unit are arranged on a bridge for ensuring a fixed, non-zero distance between the digiscope and the imaging unit in the case of a relative movement between the digiscope and the patient. As a result, the digiscope can be brought quickly from one position to another position without having to reset the distance between the imaging unit, which may be embodied as a 3D monitor, for example, and the surgeon in the process. Here, the distance between the digiscope and the imaging unit is understood to mean the distance in a horizontal direction, in particular in the viewing direction on the imaging unit. The viewing direction is understood to mean the direction from which a viewer must gaze in order to obtain an optimal impression of the illustrated image.

In particular, the bridge can include the joint which results in a compact yet at the same time flexible structure.

Furthermore, the imaging unit can be arranged on a straight line from the receptacle of the digiscope through the axis of rotation of the joint. This is advantageous in that the surgeon can assume an ergonomic body posture during an operation.

Additionally, the joint can be arranged between the digiscope and the imaging unit. As a result, the surgical microscope can have a very compact embodiment, which may be advantageous in the usually small operating theatres.

Furthermore, the joint can be arranged on a continuation of the straight line through the receptacle of the digiscope and the imaging unit, i.e., behind the imaging unit from the point of view of the digiscope. In conjunction with the joints and arms of the stand, the digiscope can be pushed to the position desired by the surgeon.

Furthermore, the distance between the digiscope and the imaging unit can lie between 0.2 meters (m) and 0.8 m and, in particular, the distance between the imaging unit and the digiscope can be adjustable. Here, the distance depends, for example, on the size and style of the employed monitor and the preferences of the surgeon. After the distance has been set, the latter can be secured, as a result of which the digiscope can be set for different surgeons. Here, setting the distance can be embodied in manual fashion or with the assistance of motors. Should the distance be set by motor, the distances can be stored in a controller and the distances stored in advance can be set, even automatically, when needed.

In one exemplary embodiment of the disclosure, the imaging unit can be mounted so as to be twistable about at least one axis perpendicular to the longitudinal axis of the bridge. As a result, it is also possible to set the angle of the imaging unit in addition to the distance and adapt these to the preference of the surgeon. Here, too, motor-driven and/or automatic setting of the imaging unit is conceivable in addition to simple manual setting.

Furthermore, the bridge can include a second joint, which divides the bridge into two segments. The receptacle of the digiscope can be arranged at the end of the first segment distant from the joint and the imaging unit can be arranged at the end of the second segment distant from the joint. The second joint allows the position between the digiscope and the imaging unit to be altered.

In particular, the two segments of the bridge divided by the joint can be embodied in such a way that they are arranged in parallel and above one another. Firstly, this can advantageously reduce the spatial requirements of the surgical microscope to a minimum, for example when the surgical microscope is not in use. Secondly, the position of the segments in relation to the second arm can be interchanged, i.e., the digiscope can be moved from one side to the side of the imaging unit and vice versa, without the bridge having to be rotated about the first joint in the process. Here, it is possible to advantageously use the space above the second arm of the stand and no additional space is required in front of the surgical microscope for changing the positions.

Additionally, the second joint can be locked in the position in which the longitudinal axes of the two segments extend parallel to the longitudinal axis of the bridge. This allows the arrangement of the digiscope and the imaging unit that is advantageous for the operation of the surgical microscope to be set easily and said arrangement is simultaneously secured in this layout. In the locked position, the bridge can then be rotated about the first joint without changing the distance and the angle of the two components with respect to one another.

Furthermore, the bridge can be embodied in such a way that it can be rotated through at least 180° without moving an arm and/or the stand. The arrangement of the digiscope and the imaging unit in relation to the stand can thus be reversed without moving the stand and/or an arm of the stand, as described further above. In the case of a new patient, this may lead to significant shortening of the conversion times and makes a movement of the stand and/or of the operating table or chair superfluous, advantageously improving the use of the available space.

A method according to an aspect of the disclosure for configuring a stand of a surgical microscope with a bridge, on which a receptacle for a digiscope and a connector for an imaging unit are disposed, wherein the bridge is mounted on an arm of the stand, at a first joint so as to be rotatable about an axis of rotation, includes the following method steps:

(a) determining a first optimal distance between eyes of a surgeon and the imaging unit;
(b) determining a second distance between the surgeon and an operating field;
(c) determining a third distance between the receptacle of the digiscope and the operating field;
(d) determining a fourth distance between the imaging unit and the receptacle of the digiscope; and
(e) determining a length of the bridge such that the distance from the surgeon to the patient and the imaging unit is optimally set for the surgeon.

In particular, the imaging unit can be embodied as a 3D screen. At a certain distance A, the 3D screen can very faithfully reproduce the images of the operating field, which were recorded by the two cameras in the digiscope and processed into a 3D image in a control unit. In this case, the optimal distance A can be set within a certain range during the production of the screen.

Furthermore, the distance between the surgeon and the operating field can be determined on the basis of the ergonomic posture during an operation and the 95% percentile of the relevant body parts of the surgeon, in particular the forearm length.

Additionally, the distance between digiscope and imaging unit can lie between 0.2 m and 0.8 m.

BRIEF DESCRIPTION OF THE DRAWINGS

The disclosure will now be described with reference to the drawings wherein:

FIG. 5 shows a flowchart of a method for configuring a stand cording to an exemplary embodiment of the disclosure.

DESCRIPTION OF EXEMPLARY EMBODIMENTS

Figure 1:
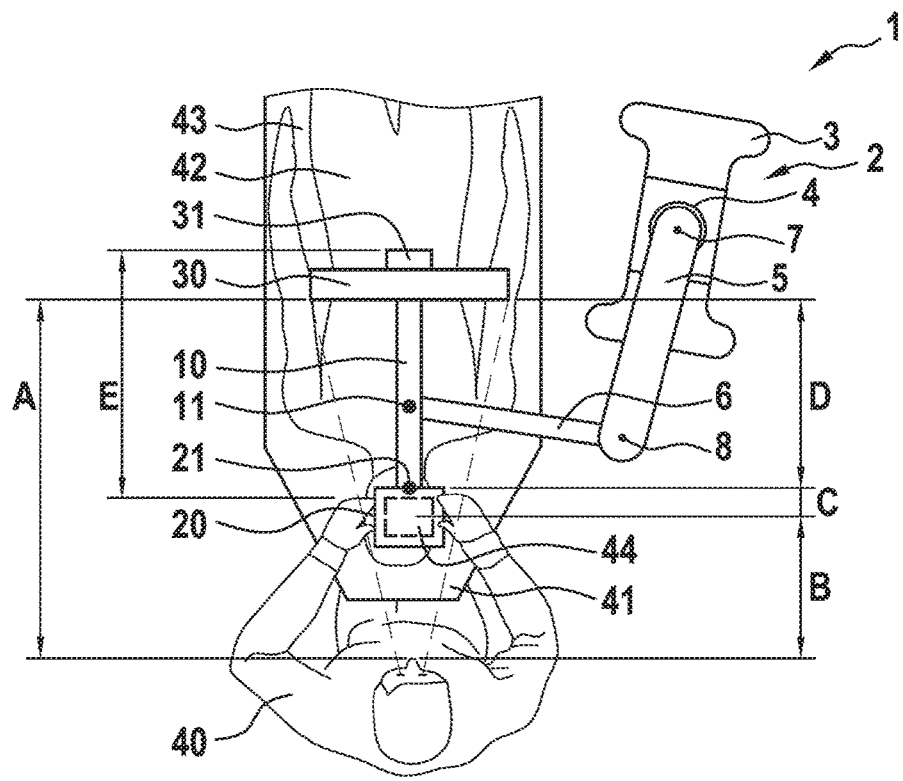
FIG. 1 shows a surgical microscope according to an exemplary embodiment of the disclosure.

FIG. 1 shows a surgical microscope 1, which includes a digital microscope, a so-called digiscope 20. Furthermore, the surgical microscope 1 includes a stand 2 with a foot 3, on which a column 4 is arranged in rotatably mounted fashion. A first end of a first arm 5, which could be embodied, for example, as a scissor arm or else as a rigid carrying arm, is arranged on the column 4 via a first stand joint 7. Here, the stand joint 7 facilitates a rotation of the arm 5 around the longitudinal axis of the column 4. Via a second stand joint 8, a first end of a second arm 6 is arranged at the other end of the first arm 5, said second arm being rotatably mounted about the stand joint 8 in the same plane as the first stand joint 7. At its second end, the second arm 6 includes a first bridge joint 11, on which a bridge 10 is rotatably mounted. A digiscope 20 in a receptacle 21 is arranged at one end of the bridge 10 and an imaging unit, embodied as a 3D screen 30, on a connector 31 is arranged at the other end of the bridge 10. The surgical microscope 1 is aligned on a patient 42 lying on a table 43 in such a way that the digiscope 20 is arranged over an operating field 44, which includes an eye (not illustrated) of the patient 42. Here, the imaging unit 30 is arranged on the bridge 10 in such a way that the viewing angle 41 and the distance A between the eyes of the surgeon 40 and the imaging unit 30, which is embodied as a 3D screen 30, are optimal. The 3D screen 30 can be embodied as an autostereoscopic or polarization-based 3D screen 30, with any other technology for 3D representation also being able to be used. Moreover, the distance B between the surgeon 40 and the operating field 44, the distance C between the operating field 44 and the receptacle 21 of the digiscope 20 and the distance D from the receptacle 21 of the digiscope 20 are illustrated, the distances being relevant in the method, described in FIG. 5, for designing the length E of the bridge. The surgical microscope 1 illustrated in FIG. 1 is only an exemplary embodiment in which the disclosure can be implemented. In other exemplary embodiments of surgical microscopes, the stand 2 can be embodied as a wall mount or ceiling mount, for example.

Figure 2:
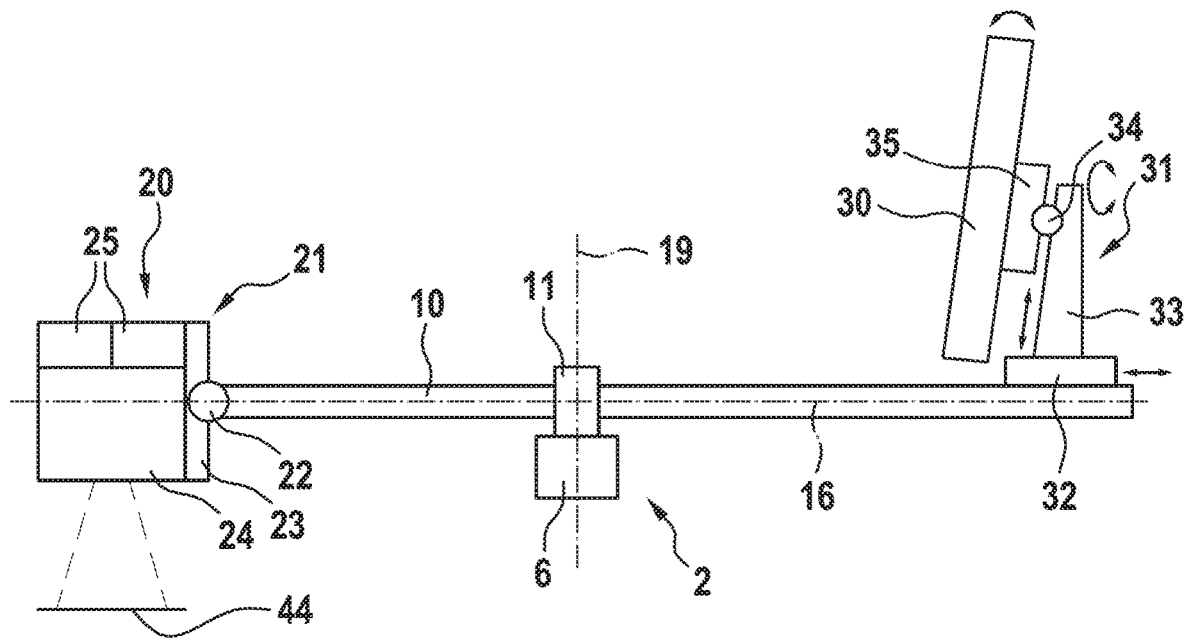
FIG. 2 shows a detailed view of the bridge.

FIG. 2 shows a detailed view of the stand 2, in which the bridge 10 is depicted on the first bridge joint 11 on the second arm 6 of the stand 2. At its one end, the bridge 10 includes the receptacle 21 for the digiscope 20, wherein the receptacle 21 comprises a joint 22 and an adapter 23, with which the digiscope 20 is fastened to the bridge 10. The joint 22 is embodied in such a way that the digiscope 20 can be twisted about the longitudinal axis 16 of the bridge 10 and about the axis, perpendicular to the longitudinal axis 16, running into the plane of the drawing. Alternatively, the digiscope 20 can also be rigidly connected to the bridge 10, with the digiscope 20 in that case being positioned by way of the kinematic mechanism of the stand 2. The digiscope 20 includes an imaging optical unit 24 and two cameras 25, which record the operating field 44 through the imaging optical unit 24. A controller, not illustrated, calculates a 3D image, which is displayed on the imaging unit 30, from the images of the two cameras 25. The connector 31 for the imaging unit 30 is arranged at the other end of the bridge 10. The connector 31 includes a carriage 32, on which the connector 31 can be moved in the direction of the longitudinal axis 16 of the bridge 10 and can be locked on the bridge 10. An arm 33 is arranged on the carriage 32, said arm being aligned substantially perpendicular to the bridge 10 and including a joint 34 at its upper end, the latter connecting the arm 33 and an adapter 35 for the imaging unit 30. The joint 34 is embodied in such a way that the imaging unit 30 can be twisted about two axes that are perpendicular to the longitudinal axis 16 of the bridge 10 and to one another. As a result, it is advantageously possible to set the distance and the lateral and vertical angles of the imaging unit 30 in relation to the surgeon (not illustrated) to the optimal values for a 3D representation. The entire bridge 10 can be moved and positioned by the kinematic mechanism provided by the joints 7 and 8 and arms 5 and 6 of the stand 2 and by a rotation of the bridge 10 about the axis of rotation 16, with the distance between the digiscope 20 and the imaging unit 30 remaining constant. Since, as a rule, the distance B between the surgeon 40 (not illustrated) and the operating field 44 is constant for a surgeon and the digiscope 20 is advantageously arranged over the operating field 44, the distance A between the eyes of the surgeon 40 (not illustrated) and the imaging unit 30 also remains at a distance and an angle optimal for the 3D imaging. As a result of the joint 22 at the receptacle 21 of the digiscope 20, the angle and the distance of the imaging unit 30 from the surgeon 40 (not illustrated) are also maintained when the surgeon 40 changes the angle between the digiscope 20 and the bridge 10.

Figure 3A:
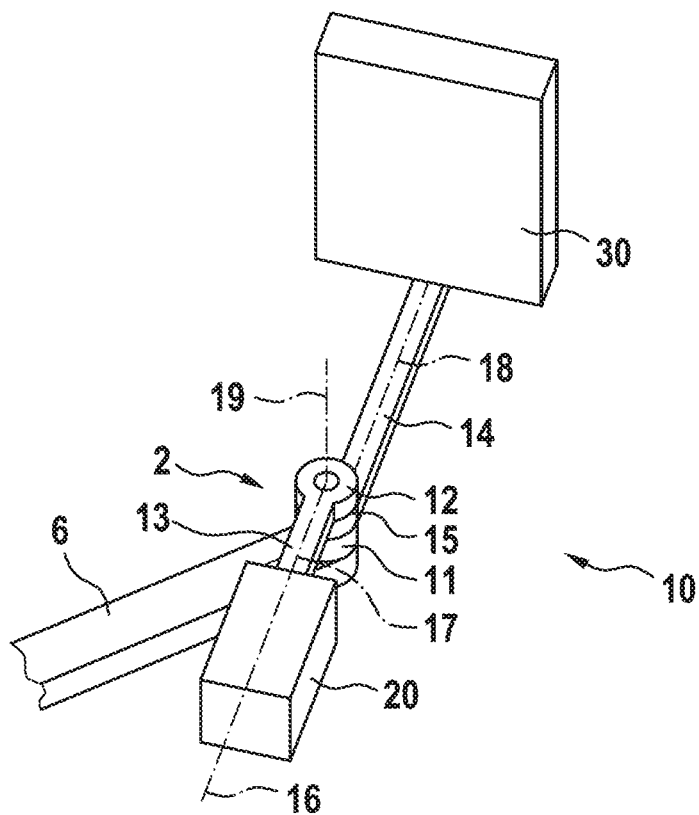
FIGS. 3A and 3B show detailed views of the bridge according to a further exemplary embodiment.
Figure 3B:
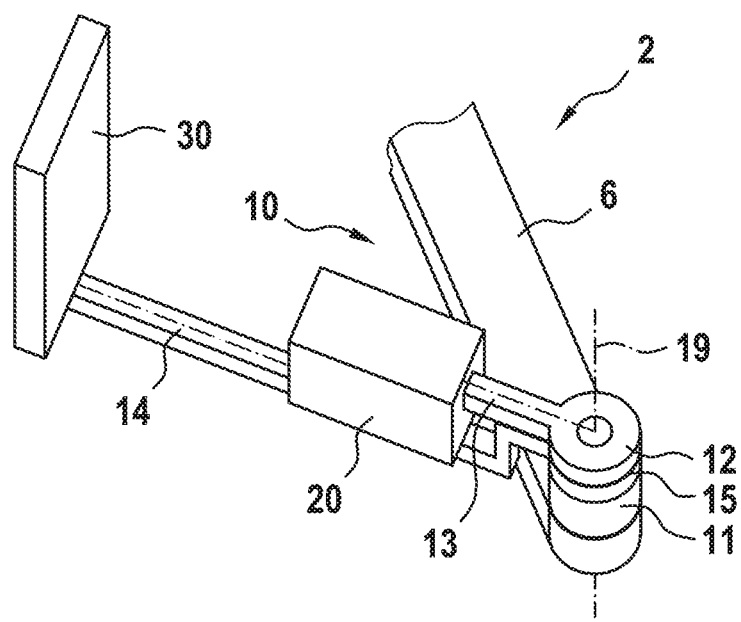

FIGS. 3A and 3B show further detailed views of the bridge 10, which is arranged with the first bridge joint 11 on the second arm 6 of the stand 2. In this exemplary embodiment, the bridge 10 includes a second bridge joint embodied as a folding joint 12, which connects a first segment 13 with the digiscope 20 to a second segment 14 with the imaging unit 30. In the shown exemplary embodiment, the second joint 12 is arranged above the first joint 11, with an arrangement in the opposite sequence also possibly being advantageous if, for example, the stand 2 is embodied as a ceiling mount. Alternatively, the second joint 12 can also be arranged at a different position of the bridge 10 than the first joint 11.

FIG. 3A shows the bridge 10 in a position in which the longitudinal axes 17 and 18 of the two segments 13 and 14 are aligned in the direction of the longitudinal axis 16 of the bridge 10 and in which the two segments include an angle of approximately 180°, i.e., in the position in which the bridge 10 with the digiscope 20 and the imaging unit 30 is advantageously aligned during an operation. The second joint 12, which is rotatable about the same axis of rotation 19 as the first joint 11, furthermore includes a locking mechanism 15, which is embodied to lock the second joint 12 in the position illustrated in FIG. 3A. The locking mechanism 15 can also be embodied for locking in further advantageous positions of the second joint 12.

FIG. 3B shows a position in which the two segments 13 and 14 with the digiscope 20 and the imaging unit 30 are arranged above one another with an identical alignment of the longitudinal axes 17 and 18, i.e., where said axes include an angle of approximately 0°. Advantageously, the locking mechanism 15 of the second joint 12 is embodied in such a way that it can also lock the joint 12 in this position, which can also be referred to as a parked position. Furthermore, the bridge 10 is embodied in such a way that, in the parked position, the two segments 13 and 14 can be swiveled about the axis of rotation 19 of the bridge over the second arm 6 of the stand 2 with the first joint 11, leading to minimal spatial requirements when the surgical microscope 1 is not in use. By way of example, this allows the surgical microscope 1 to be pushed against a wall.

Figure 4A:
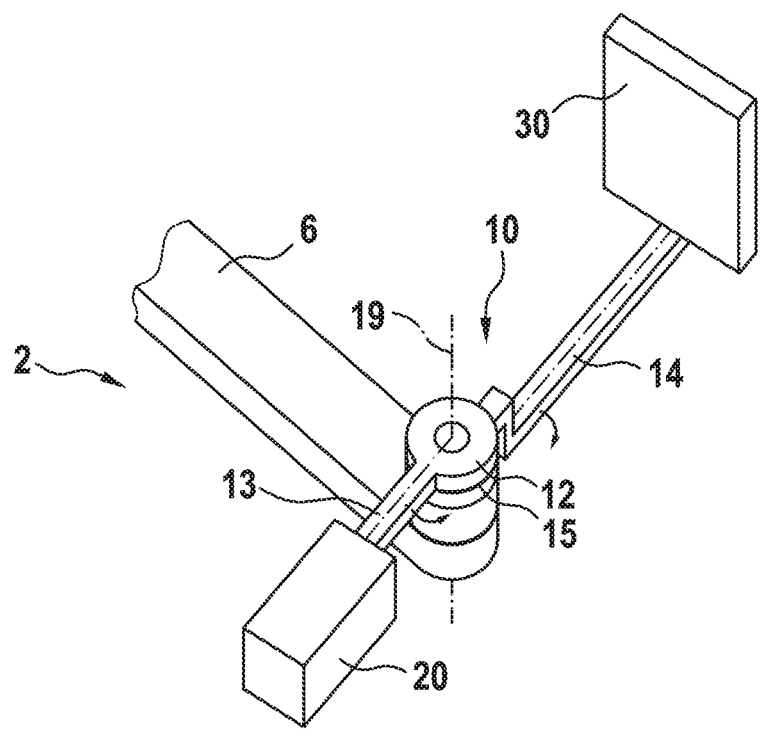
FIGS. 4A and 4B show illustrations of a 180° rotation of the digiscope and of the screen.
Figure 4B:
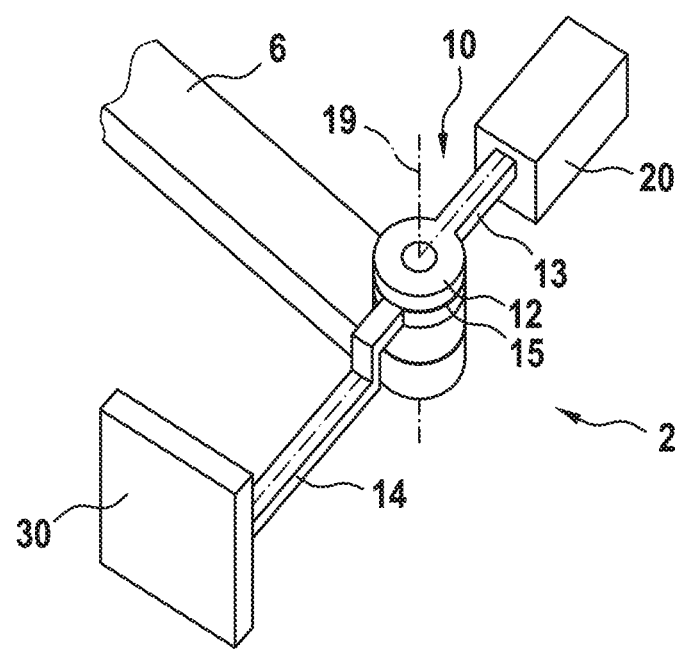

FIGS. 4A and 4B show an illustration of a 180° rotation of the digiscope 20 and of the imaging unit 30, which has to be carried out within a few minutes, for example when changing from one patient to another patient.

FIG. 4A shows the bridge 10 in an arrangement in which the digiscope 20 is arranged on the left side and the imaging unit 30 is arranged on the right side of the illustration or of the second arm 6 of the stand 2. The two segments 13 and 14 are embodied in such a way that they can be arranged above one another, i.e., the two segments can also be rotated past one another without collision. The two arrows, not labelled separately, show the directions of rotation of the two segments 13 and 14 about the axis of rotation 19 of the second bridge joint 12, in which said segments are rotated after the locking mechanism 15 of the second joint 12 was released.

FIG. 4B shows the bridge 10 following the 180° rotation, i.e., in a position in which the digiscope 20 is arranged on the right side and the imaging unit 30 is arranged on the left side of the second arm 6 of the stand 2. Here, the locking mechanism 15 is embodied in such a way that the second joint 12 can be locked in the two positions illustrated in FIGS. 4A and 4B. The segments 13 and 14 can also be embodied as shown in FIGS. 3A and 3B such that twisting through 360° about the axis of rotation 19 of the first bridge joint 11 is possible, which also facilitates a quick change of the arrangement through 180°, as shown in FIGS. 4A and 4B, without a second bridge joint 12.

FIG. 5 describes a possible method according to the disclosure for configuring a stand 2.

In a first method step 50, the optimal distance A from the eyes of the surgeon 40 to the imaging unit 30 is determined.

In a second method step 51, the distance B from the surgeon 40 to the operating field 44 is determined.

In a third method step 52, the distance C between the receptacle 21 of the digiscope 20 and the operating field 44 is determined.

In a fourth method step 53, the distance D between the imaging unit 30 and the receptacle 21 of the digiscope 20 is determined.

In a fifth method step, the length E of the bridge 10 is determined in such a way that the distance from the surgeon 40 to the patient 42 and the imaging unit 30 is optimally set for the surgeon 40.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Surgical microscope
2 Stand
3 Foot
4 Column
5 First arm
6 Second arm
7 First stand joint
8 Second stand joint
10 Bridge
11 First bridge joint
12 Second bridge joint
13 Segment (digiscope)
14 Segment (monitor)
15 Locking mechanism
16 Bridge longitudinal axis
17 Segment (digiscope) longitudinal axis
18 Segment (monitor) longitudinal axis
19 Bridge axis of rotation
20 Digital microscope (digiscope)
21 Digiscope receptacle
22 Joint receptacle
23 Adapter receptacle
24 Microscope optical unit
25 Camera
30 Screen
31 Monitor connector
32 Carriage connector
33 Arm connector
34 Joint connector
35 Bridge adapter
40 Surgeon
41 Surgeon's viewing angle
42 Patient
43 Table
44 Operating field
50 Method step 1
51 Method step 2
52 Method step 3
53 Method step 4
54 Method step 5
A Surgeon's eyes—imaging unit distance
B Surgeon—operating field distance
C Operating field—digiscope receptacle distance
D Digiscope receptacle—imaging unit distance
E Bridge length

What is claimed is:

1. A surgical microscope comprising:
a stand including an arm;
a joint defining a vertical axis of rotation;
a digiscope mounted at the joint on the arm of the stand rotatably about the vertical axis of rotation;
an imaging unit interconnected with the digiscope and mounted at the joint on the arm of the stand rotatably about the vertical axis of rotation, wherein the joint is arranged between the digiscope and the imaging unit in a horizontal direction; and
a bridge, the digiscope and the imaging unit being arranged on the bridge such that a fixed, non-zero distance between the digiscope and the imaging unit is maintained during a movement of the digiscope relative to a patient.

2. The surgical microscope according to claim 1, wherein the bridge includes the joint.

3. The surgical microscope according to claim 2, wherein:
the digiscope includes a receptacle, and
the imaging unit is arranged on a straight line from the receptacle of the digiscope through the axis of rotation of the joint.

4. The surgical microscope according to claim 3, wherein the joint is arranged on a continuation of the straight line through the receptacle of the digiscope and the imaging unit.

5. The surgical microscope according to claim 1, wherein the distance between the digiscope and the imaging unit is between 0.2 meters and 0.8 meters.

6. The surgical microscope according to claim 1, wherein the distance between the imaging unit and the digiscope is adjustable.

7. The surgical microscope according to claim 1, wherein the imaging unit is mounted twistable about at least one axis perpendicular to a longitudinal axis of the bridge.

8. The surgical microscope according to claim 1, wherein the bridge includes a second joint which divides the bridge into two segments.

9. The surgical microscope according to claim 8, wherein the two segments of the bridge divided by the second joint are embodied such that the two segments can be arranged in parallel and above one another.

10. The surgical microscope according to claim 8, wherein the second joint can be locked in a position in which longitudinal axes of the two segments extend parallel to a longitudinal axis of the bridge.

11. The surgical microscope according to claim 1, wherein the bridge is rotatable about at least 180° without moving the arm and/or the stand.

12. The surgical microscope according to claim 1, wherein the imaging unit is a 3D screen.

13. A method for configuring a stand of a surgical microscope with a bridge, on which a receptacle for a digiscope and a connector for an imaging unit are arranged, the bridge being mounted with a joint rotatably about a vertical axis of rotation defined by the joint on an arm of the stand, wherein the joint is arranged between the digiscope and the imaging unit in a horizontal direction, the method comprising:
determining a first distance between eyes of a surgeon and the imaging unit;
determining a second distance between the surgeon and an operating field;
determining a third distance between the receptacle of the digiscope and the operating field;
determining a fourth distance between the imaging unit and the receptacle of the digiscope;
determining a length of the bridge;
configuring the stand based on the first to fourth distances and the length of the bridge; and arranging the receptacle for the digiscope and the connector for the imaging unit on the bridge such that a distance from the surgeon to a patient and the imaging unit is optimally set for the surgeon.

14. Method according to claim 13, wherein the imaging unit is a 3D screen.

15. The method according to claim 13, wherein the first distance between the surgeon and the operating field is determined based on an ergonomic posture during an operation and a 95% percentile of body parts of the surgeon.

16. The method according to claim 13, wherein the first distance between the surgeon and the operating field is determined based on an ergonomic posture during an operation and a 95% percentile of a forearm length of the surgeon.

17. The method according to claim 13, wherein the distance between the digiscope and the imaging unit is between 0.2 meters and 0.8 meters.

\* \* \* \* \*